United States Patent
Hynes et al.

(10) Patent No.: US 9,526,800 B2
(45) Date of Patent: Dec. 27, 2016

(54) CANCER-RELATED EXTRACELLULAR MATRIX SIGNATURES AND RELATED METHODS AND PRODUCTS

(71) Applicants: Massachusetts Institute of Technology, Cambridge, MA (US); The General Hospital Corporation, Boston, MA (US); The Broad Institute, Inc., Cambridge, MA (US)

(72) Inventors: Richard O. Hynes, Winchester, MA (US); Alexandra Naba, Cambridge, MA (US); Karl Clauser, Boston, MA (US); Steven A. Carr, Boxford, MA (US); Kenneth Tanabe, Brookline, MA (US)

(73) Assignees: Massachusetts Institute of Technology, Cambridge, MA (US); The General Hospital Corporation, Boston, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 14/389,080

(22) PCT Filed: Mar. 14, 2013

(86) PCT No.: PCT/US2013/031492
§ 371 (c)(1),
(2) Date: Sep. 29, 2014

(87) PCT Pub. No.: WO2013/148259
PCT Pub. Date: Oct. 3, 2013

(65) Prior Publication Data
US 2015/0086565 A1    Mar. 26, 2015

Related U.S. Application Data

(60) Provisional application No. 61/616,981, filed on Mar. 28, 2012, provisional application No. 61/616,987, filed on Mar. 28, 2012.

(51) Int. Cl.

| | |
|---|---|
| *A61K 47/48* | (2006.01) |
| *A61K 38/48* | (2006.01) |
| *C07K 16/00* | (2006.01) |
| *G01N 33/574* | (2006.01) |
| *A61K 31/138* | (2006.01) |
| *A61K 31/192* | (2006.01) |
| *A61K 31/197* | (2006.01) |
| *A61K 31/215* | (2006.01) |
| *A61K 31/727* | (2006.01) |
| *C07K 16/40* | (2006.01) |
| *C12N 15/113* | (2010.01) |

(52) U.S. Cl.
CPC ....... *A61K 47/48569* (2013.01); *A61K 31/138* (2013.01); *A61K 31/192* (2013.01); *A61K 31/197* (2013.01); *A61K 31/215* (2013.01); *A61K 31/727* (2013.01); *A61K 38/486* (2013.01); *A61K 38/488* (2013.01); *A61K 38/4833* (2013.01); *A61K 47/48584* (2013.01); *A61K 47/48615* (2013.01); *C07K 16/40* (2013.01); *C12N 15/1138* (2013.01); *G01N 33/57419* (2013.01); *G01N 33/57484* (2013.01); *G01N 33/57488* (2013.01); *G01N 33/57492* (2013.01); *C12N 2310/14* (2013.01); *C12N 2310/141* (2013.01); *C12N 2320/00* (2013.01); *G01N 2333/705* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,168,146 | A | 9/1979 | Grubb et al. |
| 4,235,601 | A | 11/1980 | Deutsch et al. |
| 4,366,241 | A | 12/1982 | Tom et al. |
| 4,442,204 | A | 4/1984 | Greenquist et al. |
| 5,053,394 | A | 10/1991 | Ellestad et al. |
| 5,208,020 | A | 5/1993 | Chari et al. |
| 5,208,535 | A | 5/1993 | Nakayama et al. |

(Continued)

FOREIGN PATENT DOCUMENTS

| | | | |
|---|---|---|---|
| WO | WO 03/000203 A2 | 1/2003 | |
| WO | WO2011/028883 | * 3/2011 | ............ A61K 38/57 |

OTHER PUBLICATIONS

Mamelak et al. Phase I single-dose study of intracavitary-admininstered 131I-TM601 in adults with recurrent high-grade Glioma. J. Clin. Onc. 24, 3644-3650, 2006.*

(Continued)

*Primary Examiner* — Elly-Gerald Stoica
(74) *Attorney, Agent, or Firm* — Wolf, Greenfield & Sacks, P.C.

(57) ABSTRACT

Proteomic methods for identifying cancer related proteins and related products and kits are provided. The cancer specific proteins are extracellular matrix proteins that are associated with various aspects of cancer. Panels or signature sets of proteins useful in the detection, diagnosis and treatment of cancers as well as monitoring therapeutic progress in a cancer patient are provided herein along with methods for their detection and for their use in targeting imaging and/or therapeutic agents to the tumors via binding to the specified proteins. The proteins were identified using proteomics analyzes of tissue samples taken from cancer patients. In certain aspects the proteins are particularly useful in colon cancer patients.

8 Claims, No Drawings

(56) References Cited

U.S. PATENT DOCUMENTS

| | | | |
|---|---|---|---|
| 5,211,657 A | 5/1993 | Yamada et al. | |
| 5,770,710 A | 6/1998 | McGahren et al. | |
| 5,877,296 A | 3/1999 | Hamann et al. | |
| 2003/0157056 A1* | 8/2003 | Corti | A61K 31/70 424/85.1 |
| 2009/0068106 A1* | 3/2009 | Corti | C07K 14/78 424/9.1 |

OTHER PUBLICATIONS

Foulon et al., Preparation and Characterization of Anti-Tenascin Monoclonal Antibody-Streptavidin Conjugates for Pretargeting Applications, Bioconj. Chemistry, 10,867-876, 1999.*

Lo et al., huBC1-IL12, an immunocytokine which targets EDB-containing oncofetal fibronectin in tumors and tumor vasculature, shows potent anti-tumor activity in human tumor models. Cancer Immunol. Immunother. 56, 447-457, 2007.*

Betts et al., Chapter 14: Amino Acid Properties and Consequences of Substitutions. BioInformatics for Geneticists. John Wiley & Sons, Ltd. 2003;289-316.

Chari et al., Immunoconjugates containing novel maytansinoids: promising anticancer drugs. Cancer Res. Jan. 1, 1992;52(1):127-31.

Fraker et al., Protein and cell membrane iodinations with a sparingly soluble chloroamide, 1,3,4,6-tetrachloro-3a,6a-diphrenylglycoluril. Biochem Biophys Res Commun. Feb. 28, 1978;80(4):849-57.

Goodman et al., Integrins as therapeutic targets. Trends Pharmacol Sci. Jul. 2012;33(7):405-12. doi: 10.1016/j.tips.2012.04.002. Epub May 25, 2012. Review. 8 pages.

Naba et al., The matrisome: in silico definition and in vivo characterization by proteomics of normal and tumor extracellular matrices. Mol Cell Proteomics. Apr. 2012;11(4):M111.014647. doi: 10.1074/mcp.M111.014647. Epub Dec 9, 2011. 18 pages.

Vitetta et al., Redesigning nature's poisons to create anti-tumor reagents. Science. Nov. 20, 1987;238(4830):1098-104. Review.

Bergamaschi et al., Extracellular matrix signature identifies breast cancer subgroups with different clinical outcome. J Pathol. Feb. 2008;214(3):357-67.

Fan et al., Building prognostic models for breast cancer patients using clinical variables and hundreds of gene expression signatures. BMC Med Genomics. Jan. 9, 2011;4:3. doi: 10.1186/1755-8794-4-3.

Han et al., Selective gene transfer to endometrial cancer cells by a polymer against matrix metalloproteinase 2 (MMP-2). Cancer Biother Radiopharm. Apr. 2008;23(2):247-58. doi: 10.1089/cbr.2007.351.

Liang et al., Relationship and prognostic significance of SPARC and VEGF protein expression in colon cancer. J Exp Clin Cancer Res. Jun. 16, 2010;29:71. doi: 10.1186/1756-9966-29-71.

Mamelak et al., Phase I single-dose study of intracavitary-administered iodine-131-TM-601 in adults with recurrent high-grade glioma. J Clin Oncol. Aug. 1, 2006;24(22):3644-50.

* cited by examiner

CANCER-RELATED EXTRACELLULAR MATRIX SIGNATURES AND RELATED METHODS AND PRODUCTS

RELATED APPLICATIONS

This application is a national stage filing under U.S.C. §371 of PCT International application PCT/US2013/031492, entitled "CANCER-RELATED EXTRACELLULAR MATRIX SIGNATURES AND RELATED METHODS AND PRODUCTS," filed on Mar. 14, 2013, which claims priority under 35 U.S.C. §119(e) to U.S. Provisional Application Ser. No. 61/616,981, entitled "EXTRA CELLULAR MATRIX PROTEINS AND CANCER" filed on Mar. 28, 2012, AND to U.S. Provisional Application Ser. No. 61/616,987, entitled "CANCER SIGNATURES AND RELATED METHODS AND PRODUCTS" filed on Mar. 28, 2012, which are herein incorporated by reference in their entirety.

FEDERALLY SPONSORED RESEARCH

This invention was made with Government support under NIH U54-CA126515 and U54-CA163109. The Government has certain rights in this invention.

FIELD OF THE INVENTION

The invention relates in some aspects to application of recently developed proteomic methods for identifying cancer-related extracellular matrix (ECM) proteins correlated with cancer progression and useful for diagnosis and prognosis as well as related reagents, products and kits. The cancer-specific extracellular matrix proteins are associated with various properties of cancerous tissues. The invention also relates to ECM proteins and panels or signature sets of such proteins useful in the detection, diagnosis and treatment of cancers as well as monitoring therapeutic progress in a cancer patient. Defined lists of ECM proteins specifically expressed in primary tumors and/or in metastases and, in some cases, in metastatic primary tumors but not in non-metastatic primary tumors are presented. Thus these proteins, both individually and as sets or "signatures" can be used to determine the degree of malignancy of tumor biopsies and other samples and can be used to target specific binding reagents to tumors for purposes of imaging and therapy.

BACKGROUND OF THE INVENTION

Despite extensive study, cancer, and particularly the process of metastasis, remain major causes of illness and mortality. Prior indications suggest that changes in extracellular matrix (ECM) proteins may play significant roles in cancer progression and metastasis. The field of proteomics involves the study of proteins in complex physiological systems and their role in these systems. Large data sets have been generated using genomic and proteomic methods, but the use of that information to identify the role of extracellular matrix (ECM) proteins in disease has been limited. This is because the ECM is insoluble and crosslinked and its composition has been difficult to determine.

SUMMARY OF INVENTION

The invention in some aspects is a method involving administering to a subject having a tumor a binding reagent which interacts specifically with an extracellular matrix (ECM) protein, wherein the binding reagent is conjugated to an active agent in an effective amount to deliver the active agent to the tumor. The active agent may be or include a detectable label or a chemotherapeutic agent. The tumor may be, in some embodiments, metastatic.

In some embodiments the ECM protein is a protein selected from an ECM protein signature characteristic of non-metastatic mammary carcinoma, an ECM protein signature characteristic of metastatic mammary carcinoma, an ECM protein signature characteristic of mammary carcinoma, an ECM protein signature characteristic of metastatic primary colon carcinoma, an ECM protein signature characteristic of colon carcinoma metastases, an ECM protein signature characteristic of metastatic colon carcinoma (primary & secondary), and an ECM protein signature whose expression is associated with colon cancer or metastatic colon cancer.

In other embodiments the ECM protein is an ECM protein characteristic of metastatic tumors and is selected from an ECM protein signature characteristic of metastatic mammary carcinoma, an ECM protein signature characteristic of metastatic primary colon carcinoma, an ECM protein signature characteristic of colon carcinoma metastases, an ECM protein signature characteristic of metastatic colon carcinoma (primary & secondary), and an ECM protein signature whose expression is associated with colon cancer or metastatic colon cancer The binding reagent in other embodiments is an antibody or an antibody fragment.

The tumor in some embodiments is a tumor of the breast. The ECM protein may be selected from an ECM protein signature characteristic of metastatic mammary carcinoma. In some embodiments the ECM protein signature characteristic of metastatic mammary carcinoma is selected from subgroup 2A, subgroup 2B, and subgroup 2C.

In other embodiments the ECM protein is selected from an ECM protein signature characteristic of non-metastatic mammary carcinoma. In some embodiments the ECM protein signature characteristic of non-metastatic mammary carcinoma is a protein selected from subgroup 1A, subgroup 1B, and subgroup 1C.

In some embodiments the ECM protein is a selected from an ECM protein signature characteristic of mammary carcinoma. In other embodiments the ECM protein signature characteristic of mammary carcinoma is a protein selected from subgroup 3A, subgroup 3B, and subgroup 3C.

The tumor may be a tumor of the colon. In some embodiments the ECM protein is selected from an ECM protein signature characteristic of metastatic primary colon carcinoma. In other embodiments the ECM protein signature characteristic of metastatic primary colon carcinoma is a protein selected from subgroup 4A, subgroup 4B, and subgroup 4C. In yet other embodiments the ECM protein is selected from an ECM protein signature characteristic of colon carcinoma metastases and optionally the ECM protein signature characteristic of colon carcinoma metastases is a protein selected from subgroup 5A, subgroup 5B, and subgroup 5C. The ECM protein in other embodiments is selected from an ECM protein signature characteristic of metastatic colon carcinoma (primary & secondary). In some embodiments the ECM protein signature characteristic of metastatic colon carcinoma (primary & secondary) is a protein selected from subgroup 6A, subgroup 6B, and subgroup 6C. In yet other embodiments the ECM protein is selected from an ECM protein signature whose expression is associated with colon cancer or metastatic colon cancer. In some embodiments the ECM protein signature whose expression is associated with colon cancer or metastatic colon cancer is a protein selected from subgroup 7A, subgroup 7B, and subgroup 7C.

A composition of a binding reagent which interacts specifically with an extracellular matrix (ECM) protein, wherein the binding reagent is conjugated to an active agent is provided according to other aspects of the invention. The ECM protein may be a protein characteristic of cancers. In some embodiments the binding reagent is an antibody, and optionally is selected from the group consisting of a monoclonal antibody, a polyclonal antibody, a chimeric antibody, a humanized antibody, a human antibody, and an antibody fragment. In some embodiments the active agent is a detectable label or a chemotherapeutic agent.

In other embodiments the ECM protein is selected from an ECM protein signature characteristic of metastatic mammary carcinoma. In some embodiments the ECM protein signature characteristic of metastatic mammary carcinoma is selected from subgroup 2A, subgroup 2B, and subgroup 2C. In other embodiments the ECM protein is selected from an ECM protein signature characteristic of non-metastatic mammary carcinoma. In some embodiments the ECM protein signature characteristic of non-metastatic mammary carcinoma is a protein selected from subgroup 1A, subgroup 1B, and subgroup 1C. The ECM protein is selected from an ECM protein signature characteristic of mammary carcinoma in some embodiments. In other embodiments the ECM protein signature characteristic of mammary carcinoma is a protein selected from subgroup 3A, subgroup 3B, and subgroup 3C.

The ECM protein is selected from an ECM protein signature characteristic of metastatic primary colon carcinoma. In some embodiments the ECM protein signature characteristic of metastatic primary colon carcinoma is a protein selected from subgroup 4A, subgroup 4B, and subgroup 4C. In various embodiments the ECM protein is selected from an ECM protein signature characteristic of colon carcinoma metastases. In some embodiments the ECM protein signature characteristic of colon carcinoma metastases is a protein selected from subgroup 5A, subgroup 5B, and subgroup 5C. The ECM protein, in some embodiments, is selected from an ECM protein signature characteristic of metastatic colon carcinoma (primary & secondary). In some embodiments the ECM protein signature characteristic of metastatic colon carcinoma (primary & secondary) is a protein selected from subgroup 6A, subgroup 6B, and subgroup 6C. In other embodiments the ECM protein is selected from an ECM protein signature whose expression is associated with colon cancer or metastatic colon cancer. In some embodiments the ECM protein signature whose expression is associated with colon cancer or metastatic colon cancer is a protein selected from subgroup 7A, subgroup 7B, and subgroup 7C.

A method is provided, in aspects of the invention, for determining the presence or absence of one or more ECM proteins characteristic of metastatic carcinoma in a tumor and determining whether the cancerous tissues are metastatic based on the presence or absence of one or more ECM proteins characteristic of metastatic carcinoma. The method may further comprise treating a subject whose tumor expresses one or more of the ECM proteins characteristic of metastatic carcinoma as identified herein with an anti-cancer agent, optionally any one of the compositions described herein. The presence of one more of the ECM protein characteristic of metastatic carcinoma in the tumor indicates that the tumor is metastatic, in some embodiments. Two or more ECM protein characteristic of metastatic carcinoma may be detected in the tumor. Optionally, five or more ECM protein characteristic of metastatic carcinoma are detected in the tumor.

In some embodiments the cancer is breast cancer and the ECM protein is selected from an ECM protein signature characteristic of metastatic mammary carcinoma. In some embodiments the ECM protein signature characteristic of metastatic mammary carcinoma is selected from subgroup 2A, subgroup 2B, and subgroup 2C.

In other embodiments the tumor is a tumor of the colon. The ECM protein is selected from an ECM protein signature characteristic of metastatic primary colon carcinoma in some embodiments. In some embodiments the ECM protein signature characteristic of metastatic primary colon carcinoma is a protein selected from subgroup 4A, subgroup 4B, and subgroup 4C. In other embodiments the ECM protein is selected from an ECM protein signature characteristic of colon carcinoma metastases. In some embodiments the ECM protein signature characteristic of colon carcinoma metastases is a protein selected from subgroup 5A, subgroup 5B, and subgroup 5C. The ECM protein, in other embodiments, is selected from an ECM protein signature characteristic of metastatic colon carcinoma (primary & secondary). In some embodiments the ECM protein signature characteristic of metastatic colon carcinoma (primary & secondary) is a protein selected from subgroup 6A, subgroup 6B, and subgroup 6C. In other embodiments the ECM protein is selected from an ECM protein signature whose expression is associated with colon cancer or metastatic colon cancer. In some embodiments the ECM protein signature whose expression is associated with colon cancer or metastatic colon cancer is a protein selected from subgroup 7A, subgroup 7B, and subgroup 7C.

Optionally, the method may involve determining whether an ECM protein characteristic of non-metastatic carcinoma is present in the tumor. In some embodiments the presence of one or more of the ECM proteins characteristic of non-metastatic carcinoma in the tumor indicates that the tumor is not metastatic. In other embodiments the ECM protein is selected from an ECM protein signature characteristic of non-metastatic mammary carcinoma. In some embodiments the ECM protein signature characteristic of non-metastatic mammary carcinoma is a protein selected from subgroup 1A, subgroup 1B, and subgroup 1C.

Optionally, the tumor may be an isolated tumor sample from a subject.

In some embodiments a level of expression of the ECM protein characteristic of metastatic carcinoma is measured and is at least twice a baseline level.

In other embodiments the ECM protein characteristic of metastatic carcinoma is detected by immunohistochemistry.

The method may be a method of tracking the progression of a tumor to a metastatic state by measuring the presence or absence of one or more ECM protein characteristic of metastatic carcinoma in the tumor over time.

Alternatively, the method may involve determining whether or not a subject has metastatic cancer comprising, determining the presence or absence of a signature of ECM proteins whose expression is associated with metastatic cancer in an isolated tissue sample from a subject and determining whether the subject has metastatic cancer based on the presence or absence of the signature of ECM proteins, such that when the signature of ECM proteins is present in the isolated tissue sample the subject has metastatic cancer.

A method for monitoring progression of a tumor to a metastatic state is provided in other aspects of the invention.

The method involves measuring the presence or absence of a signature of ECM proteins in tissue samples isolated from the subject at a first time point and a second time point and determining the progression of the tumor to a metastatic state based on changes in the presence or absence of the signature of ECM proteins at the first and second time points. The method may also involve treating a subject having a signature of ECM proteins as identified herein with an anti-cancer agent, optionally any one of the compositions described herein.

In some embodiments the cancer is colon cancer. The signature of ECM proteins, in some embodiments, includes at least 2, at least 5, at least 10, at least 15, at least 20, at least 25, at least 30 or all of the proteins selected from an ECM protein signature whose expression is associated with colon cancer or metastatic colon cancer. In some embodiments the ECM protein signature whose expression is associated with colon cancer or metastatic colon cancer is a protein selected from subgroup 7A, subgroup 7B, and subgroup 7C. In other embodiments the signature of ECM proteins includes at least 2, at least 5, at least 10, at least 15, at least 20, at least 25, at least 30 or all of the proteins selected from an ECM protein signature characteristic of metastatic colon carcinoma (primary & secondary). In some embodiments the ECM protein signature characteristic of metastatic colon carcinoma (primary & secondary) is a protein selected from subgroup 6A, subgroup 6B, and subgroup 6C. In yet other embodiments the signature of ECM proteins includes at least 2, at least 5, at least 10, at least 15, at least 20, at least 25, at least 30 or all of the proteins selected from an ECM protein signature characteristic of colon carcinoma metastases. In some embodiments the ECM protein signature characteristic of colon carcinoma metastases is a protein selected from subgroup 5A, subgroup 5B, and subgroup 5C. In other embodiments the signature of ECM proteins includes at least 2, at least 5, at least 10, at least 15, at least 20, at least 25, at least 30 or all of the proteins selected from an ECM protein signature characteristic of metastatic primary colon carcinoma. In some embodiments the ECM protein signature characteristic of metastatic primary colon carcinoma is a protein selected from subgroup 4A, subgroup 4B, and subgroup 4C.

Alternatively, the cancer may be breast cancer. In some embodiments the signature of ECM proteins includes at least 2, at least 5, at least 10, at least 15, at least 20, at least 25, at least 30 or all of the proteins selected from the group consisting of an ECM protein signature characteristic of metastatic mammary carcinoma. In other embodiments the ECM protein signature characteristic of metastatic mammary carcinoma is selected from subgroup 2A, subgroup 2B, and subgroup 2C.

In yet other embodiments the signature of ECM proteins includes at least 5, at least 15, or at least 30 of the selected proteins.

The signature of ECM proteins may be a signature characteristic of metastatic carcinoma. In some embodiments when one or more of the ECM proteins characteristic of the signature of metastatic carcinoma is present at a higher level in the isolated tissue samples from the second time point the tumor has progressed to a metastatic state. In other embodiments when the signature of ECM protein characteristic of metastasis is present at a lower level in the isolated tissue samples from the second time point the tumor has regressed to a less metastatic state.

The method may further comprise the step of determining a level of expression of a signature of primary ECM proteins in the isolated tissue samples and comparing the levels of the signature of primary ECM proteins to the levels of a signature of metastasis ECM proteins.

In some embodiments the method involves administering a chemotherapeutic agent to the subject before the tissue sample is isolated from the subject at the second time point.

In other embodiments the proteins may be detected using one or more antibodies that specifically bind to the proteins using a mass spectrometry method and/or a chromatographic method or an immunohistochemical technique. The proteins are analyzed using a quantitative ELISA in other embodiments.

A kit is provided in other aspects of the invention. The kit includes a set of binding reagents which interacts specifically with a signature of ECM proteins whose expression is associated with metastatic colon or breast cancer; a set of reagents for performing an immunohistochemistry reaction using the set of binding reagents; and instructions for performing the immunohistochemistry reactions.

In some embodiments the set of binding reagents interacts specifically with at least 2, at least 5, at least 10, at least 15, at least 20, at least 25, at least 30 or all of the proteins selected from an ECM protein signature whose expression is associated with colon cancer or metastatic colon cancer. In some embodiments the ECM protein signature whose expression is associated with colon cancer or metastatic colon cancer is a protein selected from subgroup 7A, subgroup 7B, and subgroup 7C.

In some embodiments the set of binding reagents interacts specifically with at least 2, at least 5, at least 10, at least 15, at least 20, at least 25, at least 30 or all of the proteins selected from an ECM protein signature characteristic of metastatic colon carcinoma (primary & secondary), and instructions include instructions for identifying the presence of ECM proteins characteristic of metastatic colon carcinoma (primary and secondary). In some embodiments the ECM protein signature characteristic of metastatic colon carcinoma (primary & secondary) is a protein selected from subgroup 6A, subgroup 6B, and subgroup 6C.

In other embodiments the set of binding reagents interacts specifically with at least 2, at least 5, at least 10, at least 15, at least 20, at least 25, at least 30 or all of the proteins selected from an ECM protein signature characteristic of colon carcinoma metastases, and wherein the instructions include instructions for identifying the presence of ECM proteins characteristic of colon carcinoma metastases. In some embodiments the ECM protein signature characteristic of colon carcinoma metastases is a protein selected from subgroup 5A, subgroup 5B, and subgroup 5C.

The set of binding reagents interacts specifically with at least 2, at least 5, at least 10, at least 15, at least 20, at least 25, at least 30 or all of the proteins selected from an ECM protein signature characteristic of metastatic primary colon carcinoma, and wherein the instructions include instructions for identifying the presence of ECM protein characteristic of metastatic primary colon carcinoma in other embodiments. In some embodiments the ECM protein signature characteristic of metastatic primary colon carcinoma is a protein selected from subgroup 4A, subgroup 4B, and subgroup 4C.

In yet other embodiments the set of binding reagents interacts specifically with at least 2, at least 5, at least 10, at least 15, at least 20, at least 25, at least 30 or all of the proteins selected from an ECM protein signature characteristic of metastatic mammary carcinoma and wherein the instructions include instructions for identifying the presence of ECM protein characteristic of metastatic mammary carcinoma. In some embodiments the ECM protein signature characteristic of metastatic mammary carcinoma is selected from subgroup 2A, subgroup 2B, and subgroup 2C.

In some embodiments the set of binding reagents interacts specifically with at least 2, at least 5, at least 10, at least 15, at least 20, at least 25, at least 30 or all of the proteins selected from an ECM protein signature characteristic of mammary carcinoma, and wherein the instructions include instructions for identifying the presence of ECM protein characteristic of mammary carcinoma. In some embodiments the ECM protein signature characteristic of mammary carcinoma is a protein selected from subgroup 3A, subgroup 3B, and subgroup 3C.

The set of binding reagents interacts specifically with at least five, at least fifteen, or at least thirty of the selected proteins, in some embodiments.

In other aspects the invention is a method, involving administering to a subject having a tumor an extracellular matrix (ECM) protein inhibitor, wherein the ECM protein inhibitor is an inhibitor of a protein selected from any of the proteins of an ECM protein signature characteristic of non-metastatic mammary carcinoma, an ECM protein signature characteristic of metastatic mammary carcinoma, an ECM protein signature characteristic of mammary carcinoma, an ECM protein signature characteristic of metastatic primary colon carcinoma, an ECM protein signature characteristic of colon carcinoma metastases, an ECM protein signature characteristic of metastatic colon carcinoma (primary & secondary), and an ECM protein signature whose expression is associated with colon cancer or metastatic colon cancer.

In some embodiments the ECM protein is characteristic of metastatic carcinoma and is selected from an ECM protein signature characteristic of metastatic mammary carcinoma, an ECM protein signature characteristic of metastatic primary colon carcinoma, an ECM protein signature characteristic of colon carcinoma metastases, an ECM protein signature characteristic of metastatic colon carcinoma (primary & secondary), and an ECM protein signature whose expression is associated with colon cancer or metastatic colon cancer.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

DETAILED DESCRIPTION

Cancer is a complex disease, progressing from initiation of a primary tumor, typically via one or more mutational events leading to excessive growth of a primary tumor. So long as the primary tumor remains restricted to its site of origin, it is often possible to resect it surgically and it is often referred to as a benign tumor. However, further changes, both intrinsic to the tumor cells themselves and by recruitment of non-tumor cells that interact with the tumor cells (often called "stromal" cells), lead to progression in the state of the tumor eventually resulting in invasion into underlying tissues. Such tumors are referred to as invasive or malignant and are much harder to treat by surgery because it is difficult to ensure removal of all the tumor cells since they have invaded and spread. This problem is exacerbated by the process of metastasis, in which tumor cells detach from the primary tumor and migrate away from it, eventually penetrating into the vasculature and/or the lymphatics and spreading extensively through the body seeding secondary tumors or metastases at distant sites. Although some metastases can be removed surgically, they are frequently numerous, may be small and hard to detect and are therefore impossible to remove by surgery. Treatment then calls for radiotherapy or chemotherapy and, despite decades of effort, these methods remain ineffective and metastatic cancer is responsible for 90% of cancer deaths. Therefore, there is a pressing need for better understanding of the mechanisms of metastasis and the development of methods to detect and eradicate metastases.

The invention described herein offers several approaches to tackling these challenges. The focus is on a particular compartment of tumors known as the extracellular matrix (ECM), a complex meshwork of protein fibrils with associated growth factors and enzymes that provides multiple stimuli for tumor and stromal cells promoting cell proliferation and cell survival and providing substrates for cell migration and invasion and protective niches for tumor cells. These often provide survival signals to the tumor cells in the face of immune or therapeutic attack. The biochemical composition of the ECM has been difficult to define because of its very nature as a meshwork of insoluble and crosslinked fibrils that render standard biochemical analyses impossible.

The methods used according to the invention employ very recent advances in technology combining selective enrichment of the ECM, bioinformatic definition of the complete inventory of ECM proteins encoded in the genome and application of mass spectrometry. These methods have made possible the determination of the ECM complement of any tissue from small samples of tissue. This approach has revealed the striking result that any tissue contains ~150 ECM proteins and that each tissue is characterized by a specific set of ECM proteins—an ECM signature. Furthermore, the ECM signatures of primary tumors differ from those of surrounding normal tissue and those of non-metastatic primary tumors differ from those of closely related metastatic primary tumors and metastases differ from their parent primaries. Thus, it is possible to define ECM signatures characteristic of tumors in different stages of malignancy and metastatic progression. Application of these methods to human tumor samples, including specifically those of mammary and colon carcinomas has defined a series of ECM signatures characteristic of different stages in the progression of these tumors. Thus, the invention in some aspects relates to the application of new methods combining bioinformatics and mass spectrometry to characterize and compare the ECM compositions of normal human tissues, primary tumors and metastases.

We describe several methods based on application and exploitation of these signatures and the proteins therein. Methods for determining these "signatures" from patient samples and thus providing evidence as to whether those patient samples are "non-metastatic primary tumor," or "metastatic primary tumor" or "metastases". Such methods are based on the signatures defined by mass spectrometry (examples of which are listed herein) and are determined using specific sets of antibodies or similar specific probe reagents to define which proteins of the signatures are present in the samples. Methods include immunohistochemistry, ELISA, protein arrays and similar methods. Use of such methods provides diagnostic, prognostic and monitoring information allowing improved management of cancer patients' care and therapy.

Methods for targeting imaging agents (e.g., radionuclides, fluorescent reporters or other detectable reagents, etc.) specifically to individual proteins within the "signatures" to detect the location, extent and progression of primary tumors and/or metastases are also encompassed within the invention. Targeting may be by use of specific antibodies or other specific binding reagents tagged with such imaging agents.

Methods for targeting therapeutic agents (e.g., radionuclides, chemotherapeutic drugs, toxins, cytokines, etc.) specifically to individual proteins within the "signatures" in order to concentrate such therapeutic agents to primary tumors and/or metastases and thus improve therapeutic index are also aspects of the invention. Targeting of the therapeutic agents may be achieved by attaching them to specific binding reagents such as antibodies against ECM proteins defined in the aspects described above. Other aspects of the invention relate to methods for targeting functions of specific ECM proteins using specific reagents designed to interfere with their pro-metastatic functions. Examples would include blocking the interactions of ECM proteins with their receptors or with other ECM proteins (using antibodies, antibody fragments, peptides or peptidomimetics) and, in the case of ECM or ECM-associated proteins with enzymatic activities, inhibitors of those activities.

One method of the invention involves the use of signatures of ECM proteins to identify and/or characterize tissue. The signatures of ECM proteins can be used to identify the presence or absence of a type of tissue, such as cancerous tissue in a sample or in a body. For instance, a tissue sample may be isolated from the body of a subject and the signature of ECM proteins can be examined.

As used herein, an isolated tissue sample is tissue obtained from a tissue biopsy, a surgically resected tumor, or any other tumor mass removed from the body using methods well known to those of ordinary skill in the related medical arts. The tissue may be known to be cancerous or suspected of being cancerous. The phrase "suspected of being cancerous" as used herein means a cancer tissue sample believed by one of ordinary skill in the medical arts to contain cancerous cells. Methods for obtaining the sample from a biopsy include gross apportioning of a mass, microdissection, laser-based microdissection, or other art-known cell-separation methods. The tissue may also be a histological section.

Because of the variability of the cell types in diseased-tissue biopsy material, and the variability in sensitivity of the predictive methods used, the sample size required for analysis may be 5 mg, 10 mg, 15 mg, 25 mg, 30 mg, or 50 mg or greater of tissue. Alternatively it may be portions or sections of biopsy sized tissue samples. The appropriate sample size may be determined based on the cellular composition and condition of the biopsy and the standard preparative steps for this determination and subsequent isolation of the proteins for use in the invention are well known to one of ordinary skill in the art.

Alternatively, the signature of ECM proteins may be analyzed directly in a body. For instance, one or more or a panel of binding reagents such as small molecules, binding peptides or antibodies capable of recognizing one or more of the signature of ECM proteins may be administered to the subject directly. The binding reagents may be labeled in order to assist with visualization of the ECM. Alternatively, other reagents may be used to provide visualization of the ECM. In other embodiments the tissues may be removed from the subject before exposure to the binding reagents.

An ECM protein, as used herein, refers to any protein recognized as being a part of the ECM. ECM is a fundamental and important component of metazoan organisms providing architectural support and anchorage for the cells. The ECM consists of a complex meshwork of highly cross-linked proteins and exists as interstitial forms within organs and as specialized forms, such as basement membranes underlying epithelia, vascular endothelium, and surrounding certain other tissues and cell types (e.g. neurons, muscles). Cells adhere to the ECM via transmembrane receptors, among which integrins are the most prominent. These cell-matrix interactions result in the stimulation of various signaling pathways controlling proliferation and survival, differentiation, migration, etc. The composition of the ECM and the repertoire of ECM receptors determine the responses of the cells. The biophysical properties of the ECM (deformability or stiffness) have also been shown to modulate these cellular functions. In addition to core ECM components (fibronectins, collagens, laminins, proteoglycans, etc.), the ECM serves as a reservoir for growth factors and cytokines and ECM-remodeling enzymes that collaborate with ECM proteins to signal to the cells.

The methods involve the use of a ECM protein or a signature of ECM proteins. A signature of ECM proteins, as used herein, refers to a set of information useful for identifying or characterizing a tissue. The set of information includes 2 or more ECM proteins associated with that tissue. The signature or ECM proteins can be used to identify tissues in a tissue sample or it may be used to characterize the tissue. For instance the ECM protein binding reagents or signature of ECM proteins may be used to identify the metastatic potential of a tissue. It is possible to identify the degree of malignancy of a tissue by comparing different signatures of ECM proteins. For instance a method involving the screening of set of normal ECM proteins versus a set of ECM protein characteristic of metastatic carcinoma would provide information such as a weighted value for the degree of metastasis of the tissue such that the skilled artisan can determine whether a tissue is metastatic or not. Such information can be characterized in terms of a sliding scale of metastatic potential.

ECM protein binding reagents may be developed for tissues having different properties (ie. highly or poorly metastatic).

For instance, provided herein as part of the invention is a set of ECM proteins (i.e., a signature) characteristic of non-metastatic mammary carcinomas and a set of ECM proteins characteristic of metastatic mammary carcinoma. The ECM protein signature characteristic of non-metastatic carcinoma comprises proteins which are characteristic of cancerous tissues that are not metastatic, have not yet metastasized or have low metastatic potential. The ECM protein signature characteristic of non-metastatic carcinoma can be used to identify or characterize cancerous tissues that are non- or poorly metastatic. The ECM protein signature characteristic of non-metastatic mammary carcinoma of the invention is referred to as GROUP 1 and includes but is not limited to any of the following proteins: COL17A1, COL19A1, Emilin2, Itih3, LAMA2, PLAT (tPA), THBS2, TNXB, Aspn, Col28a1, COL6A6, EMID2, FBLN5, FLG2, Gm7455, Hmcn1, Lum, MMP1, MMP19, NGLY1, OGN, PRELP, S100A16, S100A8, Timp3, Vwa1, COL25A1, HRNR, ITIH5, and MMP2. In some embodiments, the ECM protein signature characteristic of non-metastatic mammary carcinoma does not include MMP2 and, or S100A8.

In other embodiments the ECM protein signature characteristic of non-metastatic mammary carcinoma is referred to as subgroup 1A and includes 1 or more of the following proteins: COL17A1, COL19A1, Emilin2, Itih3, LAMA2, PLAT (tPA), THBS2, TNXB, Aspn, Col28a1, COL6A6, EMID2, FBLN5, FLG2, Gm7455, Hmcn1, Lum, MMP1, MMP19, NGLY1, OGN, PRELP, S100A16, S100A8, Timp3, and Vwa1. In some embodiments, the ECM protein signature characteristic of non-metastatic mammary carcinoma does not include S100A8.

In other embodiments the ECM protein signature characteristic of non-metastatic mammary carcinoma is referred to as subgroup 1B and includes 1 or more of the following proteins: COL17A1, COL19A1, Emilin2, Itih3, LAMA2, PLAT (tPA), THBS2, and TNXB.

In other embodiments the ECM protein signature characteristic of non-metastatic mammary carcinoma is referred to as subgroup 1C and includes 1 or more of the following proteins: Aspn, Col28a1, COL6A6, EMID2, FBLN5, FLG2, Gm7455, Hmcn1, Lum, MMP1, MMP19, NGLY1, OGN, PRELP, S100A16, S100A8, Timp3, and Vwa1. In some embodiments, the ECM protein signature characteristic of non-metastatic mammary carcinoma does not include S100A8.

The ECM proteins characteristic of metastatic mammary carcinoma are proteins which are characteristic of cancerous tissues that are metastatic or have high metastatic potential. These ECM proteins characteristic of metastatic carcinoma can be used to identify or characterize cancerous tissue that is metastatic or highly metastatic. The ECM protein signature characteristic of metastatic mammary carcinoma of the invention is referred to as GROUP 2 and includes but is not limited to any of the following proteins: C1qc, CTSB, CTSF, EGLN1, F10, F13b, LTBP3, S100A2, SNED1, SRPX, TIMP1, Vwf, ADAM10, ADAM9, AGRN, ANGPTL4, C1qa, COL22A1, COL24A1, COL4A6, CST3, CTGF, CTSC, EFEMP2, Habp2, HCFC2, HTRA1, IGFBP4, I116, Itih4, LEPREL2, LOXL2, MFGE8, P4HTM, Papln, Plxnb2, PRG4, S100A10, Serpina1b, SERPINC1, SERPINE2, Serpinf1, TINAGL1, BMP1, COL23A1, CYR61, LAMC2, LOX, SERPINA1, WNT5B. In some embodiments the ECM proteins characteristic of metastatic mammary carcinoma are not one or more of: CTSB, ANGPTL4, CTGF, LOXL2, CYR61, LOX.

In other embodiments the ECM protein characteristic of metastatic mammary carcinoma is referred to as subgroup 2A and includes 1 or more of the following proteins: C1qc, CTSB, CTSF, EGLN1, F10, F13b, LTBP3, S100A2, SNED1, SRPX, TIMP1, Vwf, ADAM10, ADAM9, AGRN, ANGPTL4, C1qa, COL22A1, COL24A1, COL4A6, CST3, CTGF, CTSC, EFEMP2, Habp2, HCFC2, HTRA1, IGFBP4, I116, Itih4, LEPREL2, LOXL2, MFGE8, P4HTM, Papln, Plxnb2, PRG4, S100A10, Serpina1b, SERPINC1, SERPINE2, Serpinf1, and TINAGL1. In some embodiments the ECM proteins characteristic of metastatic mammary carcinoma are not one or more of: CTSB, ANGPTL4, CTGF, LOXL2.

In other embodiments the ECM proteins characteristic of metastatic mammary carcinoma are referred to as subgroup 2B and include 1 or more of the following proteins: C1qc, CTSB, CTSF, EGLN1, F10, F13b, LTBP3, S100A2, SNED1, SRPX, TIMP1, and Vwf. In some embodiments the ECM protein characteristic of metastatic mammary carcinoma is not CTSB.

In other embodiments the ECM protein signature characteristic of metastatic mammary carcinoma is referred to as subgroup 2C and includes 1 or more of the following proteins: ADAM10, ADAM9, AGRN, ANGPTL4, C1qa, COL22A1, COL24A1, COL4A6, CST3, CTGF, CTSC, EFEMP2, Habp2, HCFC2, HTRA1, IGFBP4, I116, Itih4, LEPREL2, LOXL2, MFGE8, P4HTM, Papln, Plxnb2, PRG4, S100A10, Serpina1b, SERPINC1, SERPINE2, Serpinf1, and TINAGL1. In some embodiments the ECM protein characteristic of metastatic mammary carcinoma are not one or more of: ANGPTL4, CTGF, LOXL2.

In yet other embodiments the ECM protein signature characteristic of mammary carcinoma comprises one or more proteins included in any of the groups above. The ECM protein signature characteristic of mammary carcinoma of the invention is referred to as GROUP 3 and includes but is not limited to any of the following proteins: COL17A1, COL19A1, Emilin2, Itih3, LAMA2, PLAT (tPA), THBS2, TNXB, Aspn, Col28a1, COL6A6, EMID2, FBLN5, FLG2, Gm7455, Hmcn1, Lum, MMP1, MMP19, NGLY1, OGN, PRELP, S100A16, S100A8, Timp3, Vwa1, COL25A1, HRNR, ITIH5, MMP2, C1qc, CTSB, CTSF, EGLN1, F10, F13b, LTBP3, S100A2, SNED1, SRPX, TIMP1, Vwf, ADAM10, ADAM9, AGRN, ANGPTL4, C1qa, COL22A1, COL24A1, COL4A6, CST3, CTGF, CTSC, EFEMP2, Habp2, HCFC2, HTRA1, IGFBP4, I116, Itih4, LEPREL2, LOXL2, MFGE8, P4HTM, Papln, Plxnb2, PRG4, S100A10, Serpina1b, SERPINC1, SERPINE2, Serpinf1, TINAGL1, BMP1, COL23A1, CYR61, LAMC2, LOX, SERPINA1, WNT5B. In some embodiments the mammary ECM protein is not one or more of: S100A8, MMP2, CTSB, ANGPTL4, CTGF, LOXL2, CYR61, LOX.

In other embodiments the ECM protein signature characteristic of mammary carcinoma is referred to as subgroup 3A and includes 1 or more of the following proteins: COL17A1, COL19A1, Emilin2, Itih3, LAMA2, PLAT (tPA), THBS2, TNXB, Aspn, Col28a1, COL6A6, EMID2, FBLN5, FLG2, Gm7455, Hmcn1, Lum, MMP1, MMP19, NGLY1, OGN, PRELP, S100A16, S100A8, Timp3, Vwa1, C1qc, CTSB, CTSF, EGLN1, F10, F13b, LTBP3, S100A2, SNED1, SRPX, TIMP1, Vwf, ADAM10, ADAM9, AGRN, ANGPTL4, C1qa, COL22A1, COL24A1, COL4A6, CST3, CTGF, CTSC, EFEMP2, Habp2, HCFC2, HTRA1, IGFBP4, I116, Itih4, LEPREL2, LOXL2, MFGE8, P4HTM, Papln, Plxnb2, PRG4, S100A10, Serpina1b, SERPINC1, SERPINE2, Serpinf1, and TINAGL1. In some embodiments the mammary ECM proteins of subgroup 3A are not one or more of S100A8, CTSB, ANGPTL4, CTGF, LOXL2.

In other embodiments the ECM protein signature characteristic of mammary carcinoma is referred to as subgroup 3B and includes 1 or more of the following proteins: COL17A1, COL19A1, Emilin2, Itih3, LAMA2, PLAT (tPA), THBS2, TNXB, C1qc, CTSB, CTSF, EGLN1, F10, F13b, LTBP3, S100A2, SNED1, SRPX, TIMP1, and Vwf. In some embodiments the mammary ECM protein of subgroup 3B is not S100A8.

In other embodiments the ECM protein signature characteristic of mammary carcinoma is referred to as subgroup 3C and includes 1 or more of the following proteins: Aspn, Col28a1, COL6A6, EMID2, FBLN5, FLG2, Gm7455, Hmcn1, Lum, MMP1, MMP19, NGLY1, OGN, PRELP, S100A16, S100A8, Timp3, Vwa1, ADAM10, ADAM9, AGRN, ANGPTL4, C1qa, COL22A1, COL24A1, COL4A6, CST3, CTGF, CTSC, EFEMP2, Habp2, HCFC2, HTRA1, IGFBP4, I116, Itih4, LEPREL2, LOXL2, MFGE8, P4HTM, Papln, Plxnb2, PRG4, S100A10, Serpina1b, SERPINC1, SERPINE2, Serpinf1, and TINAGL1. In some embodiments the mammary ECM proteins of subgroup 3C are not one or more of S100A8, ANGPTL4, CTGF, LOXL2.

Also provided herein is a signature of ECM proteins whose expression is associated with metastatic colon carcinoma. This signature is a set of ECM proteins that specifically identifies cancerous tissue in a subject or that has been isolated from a subject that has colon carcinoma. This signature specifically identifies these tissues because the ECM proteins within this signature are present in any of the cancerous tissues from a patient with metastases (primary tumor, secondary tumor—or metastases-, or both), and are not present on a normal non-cancerous tissues.

An exemplary signature of ECM proteins whose expression is associated with colon cancer or metastatic colon cancer is at least 1 or 2 proteins identified below as being an ECM protein signature characteristic of metastatic primary colon carcinoma, an ECM protein signature characteristic of colon carcinoma metastases, or an ECM protein signature characteristic of metastatic colon carcinoma (primary & secondary), referred as GROUP 7, and comprising 1 or more of the following proteins: ADAM10, CLEC11A, FGL2, LOXL1, MFGE8, MMP9, MMRN1, MUC13, PAPLN, PLOD3, PLXNB2, S100A16, ADAM9, ADAMTSL1, C15orf44, CSPG4, EMID1, FCN1, FMOD, LEFTY1, LEPRE1, MEGF8, MMP1, MMP11, MMP12, MMP2, MMRN2, PLOD2, PLXDC2, PLXND1, S100A11, S100A14, SERPINA3, SERPINF1, SPARC, SVEP1, TGFB1, ADAMDEC1, ANXA13, ANXA7, COL8A1, GREM1, INHBE, LEFTY2, LTBP3, LTBP4, MATN2, MFAP4, MUC5B, THSD4, COMP, HPX, IGFALS, SPP1, BMP1, C1QTNF5, FNDC1, ANXA3, C1QC, CCL21, COL10A1, COL15A1, COL27A1, CRLF3, CTSA, CTSH, CXCL12, F12, FCN3, HABP2, IL16, ITIH2, KNG1, LAMA3, LEFTY1, MMP12, MMP7, MST1, NID1, PCOLCE, PRG4, S100A12, S100A4, S100P, SERPINA1, SERPINA3, SERPINB5, SERPINB6, SERPINB9, SERPINC1, SERPIND1, SERPING1, THBS1, ANXA5, HCFC1, HTRA1, LTBP2, MXRA5, ST14, COL22A1, GPC4, LOXL2, MUC16, PXDN, SFTPD, THBS2, C1QA, C1QB, F2, PLOD1, SERPINB1, TIMP1, AGRN, EFEMP2, HMCN1, SERPINE2, A2M, AEBP1, ANXA1, ANXA11, ANXA4, ANXA6, COL18A1, COL4A1, CSTB, CTSB, CTSD, ECM1, ELANE, F9, FCN1, HRG, IGFBP7, ITIH1, ITIH4, LAMB3, LAMC2, LGALS9, LMAN1, PLG, S100A11, S100A6, S100A8, S100A9, SERPINF1, and SERPINH1. In some embodiments, the ECM protein signature characteristic of colon carcinoma does not include one or more of: MMP9, MMP2, SPARC, TGFB1, SPP1, LOXL2, CTSB and/or S100A8.

In other embodiments the ECM protein signature characteristic of colon carcinoma is referred to as subgroup 7A and includes 1 or more of the following proteins: ADAM10, CLEC11A, FGL2, LOXL1, MFGE8, MMP9, MMRN1, MUC13, PAPLN, PLOD3, PLXNB2, S100A16, ADAM9, ADAMTSL1, C15orf44, CSPG4, EMID1, FCN1, FMOD, LEFTY1, LEPRE1, MEGF8, MMP1, MMP11, MMP12, MMP2, MMRN2, PLOD2, PLXDC2, PLXND1, S100A11, S100A14, SERPINA3, SERPINF1, SPARC, SVEP1, TGFB1, COMP, HPX, IGFALS, SPP1, BMP1, C1QTNF5, FNDC1, ANXA5, HCFC1, HTRA1, LTBP2, MXRA5, ST14, COL22A1, GPC4, LOXL2, MUC16, PXDN, SFTPD, and THBS2. In some embodiments the colon carcinoma ECM protein signature does not include one or more of: MMP9, MMP2, SPARC, TGFB1, SPP1, LOXL2.

In other embodiments, the ECM protein signature characteristic of colon carcinoma is referred to as subgroup 7B and includes 1 or more of the following proteins: ADAM10, CLEC11A, FGL2, LOXL1, MFGE8, MMP9, MMRN1, MUC13, PAPLN, PLOD3, PLXNB2, S100A16, COMP, HPX, IGFALS, SPP1, ANXA5, HCFC1, HTRA1, LTBP2, MXRA5, and ST14. In some embodiments the colon carcinoma ECM protein is not MMP9 and/or SPP1.

In other embodiments, the ECM protein signature characteristic of colon carcinoma is referred to as subgroup 7C and includes 1 or more of the following proteins: ADAM9, ADAMTSL1, C15orf44, CSPG4, EMID1, FCN1, FMOD, LEFTY1, LEPRE1, MEGF8, MMP1, MMP11, MMP12, MMP2, MMRN2, PLOD2, PLXDC2, PLXND1, S100A11, S100A14, SERPINA3, SERPINF1, SPARC, SVEP1, TGFB1, BMP1, C1QTNF5, FNDC1, COL22A1, GPC4, LOXL2, MUC16, PXDN, SFTPD, and THBS2. In some embodiments the colon carcinoma ECM protein is not MMP2, SPARC, TGFB1 and/or LOXL2.

The signature of ECM proteins may also be an ECM protein signature characteristic of metastatic primary colon carcinoma. An exemplary ECM protein signature characteristic of metastatic primary colon carcinoma is referred to as GROUP 4 and includes 1 or more of the following proteins: ADAM10, CLEC11A, FGL2, LOXL1, MFGE8, MMP9, MMRN1, MUC13, PAPLN, PLOD3, PLXNB2, S100A16, ADAM9, ADAMTSL1, C15orf44, CSPG4, EMID1, FCN1, FMOD, LEFTY1, LEPRE1, MEGF8, MMP1, MMP11, MMP12, MMP2, MMRN2, PLOD2, PLXDC2, PLXND1, S100A11, S100A14, SERPINA3, SERPINF1, SPARC, SVEP1, TGFB1, ADAMDEC1, ANXA13, ANXA7, COL8A1, GREM1, INHBE, LEFTY2, LTBP3, LTBP4, MATN2, MFAP4, MUC5B, and THSD4. In some embodiments the ECM protein signature characteristic of metastatic primary colon carcinomas does not include MMP9, MMP2, SPARC and/or TGFB1.

In other embodiments the ECM protein signature characteristic of metastatic primary colon carcinoma is referred to as subgroup 4A and include 1 or more of the following proteins: ADAM10, CLEC11A, FGL2, LOXL1, MFGE8, MMP9, MMRN1, MUC13, PAPLN, PLOD3, PLXNB2, S100A16, ADAM9, ADAMTSL1, C15orf44, CSPG4, EMID1, FCN1, FMOD, LEFTY1, LEPRE1, MEGF8, MMP1, MMP11, MMP12, MMP2, MMRN2, PLOD2, PLXDC2, PLXND1, S100A11, S100A14, SERPINA3, SERPINF1, SPARC, SVEP1, and TGFB1. In some embodiments the ECM protein signature characteristic of metastatic primary colon carcinomas does not include: MMP9, MMP2, SPARC and/or TGFB1.

In other embodiments the ECM protein signature characteristic of metastatic primary colon carcinoma is referred to as subgroup 4B and includes 1 or more of the following proteins: ADAM10, CLEC11A, FGL2, LOXL1, MFGE8, MMP9, MMRN1, MUC13, PAPLN, PLOD3, PLXNB2, and S100A16. In some embodiments the ECM protein characteristic of metastatic primary colon carcinomas is not MMP9.

In other embodiments the ECM protein signature characteristic of metastatic primary colon carcinoma is referred to as subgroup 4C and include 1 or more of the following proteins: ADAM9, ADAMTSL1, C15orf44, CSPG4, EMID1, FCN1, FMOD, LEFTY1, LEPRE1, MEGF8, MMP1, MMP11, MMP12, MMP2, MMRN2, PLOD2, PLXDC2, PLXND1, S100A11, S100A14, SERPINA3, SERPINF1, SPARC, SVEP1, and TGFB1. In some embodiments the ECM protein signature characteristic of metastatic primary colon carcinoma does not include MMP2, SPARC and/or TGFB1.

The signature of ECM proteins may also be an ECM protein signature characteristic of colon carcinoma metastases. The ECM protein signature characteristic of colon carcinoma metastases is a set of proteins that specifically identify tumors that have metastasized to a site remote from the primary tumor. For instance the tumor may be a liver metastasis of a primary colon tumor. An exemplary ECM protein signature characteristic of colon carcinoma metastases whose expression is associated with the metastatic process of colon cancer is referred to as GROUP 5 and includes 1 or more of the following proteins: COMP, HPX, IGFALS, SPP1, BMP1, C1QTNF5, FNDC1, ANXA3, C1QC, CCL21, COL10A1, COL15A1, COL27A1, CRLF3, CTSA, CTSH, CXCL12, F12, FCN3, HABP2, IL16, ITIH2, KNG1, LAMA3, LEFTY1, MMP12, MMP7, MST1, NID1, PCOLCE, PRG4, S100A12, S100A4, S100P, SERPINA1, SERPINA3, SERPINB5, SERPINB6, SERPINB9, SERPINC1, SERPIND1, SERPING1, and THBS1.

In other embodiments the ECM protein signature characteristic of colon carcinoma metastases is referred to as subgroup 5A and includes 1 or more of the following proteins: COMP, HPX, IGFALS, SPP1, BMP1, C1QTNF5, and FNDC1. In some embodiments the ECM protein signature characteristic of colon carcinoma metastases does not include SPP1.

In other embodiments the ECM protein signature characteristic of colon carcinoma metastases is referred to as subgroup 5B and includes 1 or more of the following proteins: COMP, HPX, IGFALS, and SPP1. In some embodiments the ECM protein signature characteristic of colon carcinoma metastases does not include SPP1.

In other embodiments the ECM protein signature characteristic of colon carcinoma metastases is referred to as subgroup 5C and includes 1 or more of the following proteins: BMP1, C1QTNF5, and FNDC1.

Additionally, the signature of ECM proteins may also be an ECM protein signature that specifically marks metastatic colon carcinoma (both primary tumors and the secondary tumors or metastases deriving from the primary tumors) and is referred to herein as of ECM protein signature characteristic of metastatic colon carcinoma (primary & secondary) and as GROUP 6. An exemplary signature of ECM protein signature characteristic of metastatic colon carcinoma (primary & secondary) includes 1 or more of the following proteins: ANXA5, HCFC1, HTRA1, LTBP2, MXRA5, ST14, COL22A1, GPC4, LOXL2, MUC16, PXDN, SFTPD, THBS2, C1QA, C1QB, F2, PLOD1, SERPINB1, TIMP1, AGRN, EFEMP2, HMCN1, SERPINE2, A2M, AEBP1, ANXA1, ANXA11, ANXA4, ANXA6, COL18A1, COL4A1, CSTB, CTSB, CTSD, ECM1, ELANE, F9, FCN1, HRG, IGFBP7, ITIH1, ITIH4, LAMB3, LAMC2, LGALS9, LMAN1, PLG, S100A11, S100A6, S100A8, S100A9, SERPINF1, and SERPINH1. In some embodiments, the ECM protein signature characteristic of metastatic colon carcinoma does not include CTSB and/or S100A8.

In other embodiments the ECM protein signature characteristic of metastatic colon carcinoma (primary & secondary) is referred to as subgroup 6A and includes 1 or more of the following proteins: ANXA5, HCFC1, HTRA1, LTBP2, MXRA5, ST14, COL22A1, GPC4, LOXL2, MUC16, PXDN, SFTPD, and THBS2. In some embodiments, the ECM protein signature characteristic of metastatic colon carcinoma does not include LOXL2.

In other embodiments the ECM protein signature characteristic of metastatic colon carcinoma (primary & secondary) is referred to as subgroup 6B includes 1 or more of the following proteins: ANXA5, HCFC1, HTRA1, LTBP2, MXRA5, and ST14

In other embodiments the ECM protein signature characteristic of metastatic colon carcinoma (primary & secondary) is referred to as subgroup 6C and includes 1 or more of the following proteins: COL22A1, GPC4, LOXL2, MUC16, PXDN, SFTPD, and THBS2. In some embodiments, the ECM protein signature characteristic of metastatic colon carcinoma does not include LOXL2.

In some embodiments the signature of ECM proteins includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, or 112 proteins or at least any of the recited numbers of proteins from the above lists.

A signature is a unique group of proteins identifying a particular characteristic of a tissue. While one or more of the proteins on each of the above lists may have been previously associated with a particular tissue characteristic, the unique combination or signature of each of the above lists or sub-lists is novel. Within each list or subgroup presented above various combinations of more than 2, 3, 4, 5, 6, 7, 8, 9, 10, 11, 12, 13, 14, 15, 16, 17, 18, 19, or 20 of the proteins within each list or subgroup form a signature.

The full protein sequences for each of the identified ECM proteins are known in the art. Detailed information on each of these proteins including genomic information, and listing of sources for nucleotide and protein sequences for each of these proteins is provided in the lists above in the form of ENTREZ GENE SYMBOL. The full sequences can be identified by accessing any of these accession numbers in the National Center for Biotechnology Information website: http://www.ncbi.nlm.nih.gov. As these proteins are well known to the skilled artisan, the signatures of ECM proteins and binding reagents described herein include variations and modifications to the sequences as well. The methods of the invention result in the first detailed description of the composition of the tumor extracellular matrix at the protein level and highlight many proteins of potential importance for metastatic disease. This information provides a unique opportunity to analyze and characterize the metastatic potential of tumors. In particular, the findings of the invention can be utilized to examine changes in metastatic state of tumors with time and/or in response to therapeutic interventions. In order to achieve these methods tissue samples may be isolated from a subject at different times with or without drug treatments. The different tissue samples can be analyzed for the presence of the ECM protein or signature proteins. Then the differences in ECM protein expression between the two samples can be assessed. The differences can be analyzed qualitatively (e.g. by immunohistochemistry, IHC) through assessment of the different proteins present or quantitatively by measuring levels or approximate levels of protein expression. Alternatively the methods of the invention may also be performed in vivo without removal of a tissue sample.

The presence of a protein in a tissue sample or the level of a protein in a tissue sample may be assessed using any known methods in the art. Such methodology is well known. A method commonly used in clinical and pathological assessment is immunohistochemistry, which allows determination of the presence of particular proteins or sets of proteins (such as those in a signature) in a tissue sample. Knowledge of signatures allows multiplex qualitative comparisons among tissue samples, enhancing the diagnostic and prognostic power. The methods of immunohistochemistry are well known and widely practiced. When a quantitative assessment of protein levels is made, the levels of protein may be compared with either a reference or threshold amount or with amounts found in other samples. For instance, if the presence or levels of proteins are measured in a primary tumor and its metastasis or a corresponding normal tissue, those can be compared to provide a relative assessment of the metastatic potential of the tumor. Alternatively the levels may be compared with an amount that is known (or is shown) to be an amount above or below which a tumor normally expresses the protein. The value that is used in the comparison is referred to as the reference or threshold level.

The actual numbers in the particular determination of threshold values may vary for different tumors or under different circumstances, such as the conditions of the assay to determine expression. However, the skilled artisan would be able to identify the correct threshold values based on the circumstances. For example threshold values could easily be generated using normal non-cancerous tissue under similar circumstances.

The reference sample can be any of a variety of biological samples against which a diagnostic assessment may be made. Examples of reference samples include biological samples from control populations or control samples. Reference samples may be generated through manufacture to be supplied for testing in parallel with the test samples, e.g., reference sample may be supplied in diagnostic kits. Appropriate reference samples will be apparent to the skilled artisan.

In other embodiments, the expression level of the protein in the test sample may be determined based on a direct comparison to a reference level in absolute values. For instance, at least 10%, at least 20%, at least 50%, at least 100%, at least 200%, at least 500%, at least 1000% or more higher than the expression level of the protein in the reference sample. In other embodiments, the expression level of the protein in the test sample is at least 10%, at least 20%, at least 50%, at least 100%, at least 200%, at least 500%, at least 1000% or more lower than the expression level of the protein in the reference sample.

The presence/absence or levels of proteins or markers may be determined using any of a number of techniques available to the person of ordinary skill in the art for protein analysis, e.g., direct physical measurements (e.g., mass spectrometry), binding assays (e.g., immunohistochemistry, immunoassays, agglutination assays, and immunochromatographic assays) etc. The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring protein levels may use solid phase or homogenous formats. Suitable assay methods include sandwich or competitive binding assays. Examples of sandwich immunoassays are described in U.S. Pat. No. 4,168,146 to Grubb et al. and U.S. Pat. No. 4,366,241 to Tom et al., both of which are incorporated herein by reference. Examples of competitive immunoassays include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

Multiple ECM proteins may be measured using a multiplexed assay format, e.g., multiplexing through the use of binding reagent arrays, multiplexing using spectral discrimination of labels, multiplexing by flow cytometric analysis of binding assays carried out on particles (e.g., using the Luminex system). Thus, in some embodiments the invention encompasses arrays of peptide based detection reagents for assaying 5 or more, 10 or more, 20 or more, 30 or more, 40 or more, 50 or more, or 100 or more binding reagents for binding to the proteins listed in Groups 1 to 7 otherwise described herein.

Detection of a protein in a test sample involves routine methods. The skilled artisan can detect the presence or absence of a protein using well known methods. Such methods include diverse immunoassays. In general, immunoassays involve the binding of antibodies or similar probes to proteins in a sample such a histological section or binding of proteins in a sample to a solid phase support such as a plastic surface. Detectable antibodies are then added which selectively bind to the protein of interest. Detection of the antibody indicates the presence of the protein. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in Immunoassays for the 80's, A. Voller et al., Eds., University Park, 1981, which is incorporated herein by reference.

Simple immunoassays such as a dot blot and a Western blot involve the use of a solid phase support which is contacted with a test sample. Any proteins present in the test sample bind the solid phase support and can be detected by a specific, detectable antibody preparation. The intensity of the signal can be measured to obtain a quantitative readout. Other more complex immunoassays include forward assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, in a forward sandwich assay a third detectable antibody, which binds the second antibody is added to the system. Other types of immunometric assays include simultaneous and reverse assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional assays. A reverse assay involves the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody.

A number of methods are well known for the detection of antibodies. For instance, antibodies can be detectably labeled by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Labels include any known labels that can be used with imaging techniques, such as PET isotopes, scintigraphy, NMR, etc. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, nanoparticles, etc. The label may be bound to a reagent during or following its synthesis. There are many different labels and methods of labeling known to those of ordinary skill in the art. Examples of the types of labels that can be used in the present invention include enzymes, radioisotopes, fluorescent compounds, colloidal metals, nanoparticles, chemiluminescent compounds, and bioluminescent compounds. Those of ordinary skill in the art will know of other suitable labels for the reagents described herein, or will be able to ascertain such, using routine experimentation. Furthermore, the coupling or conjugation of these labels to the reagents of the invention can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the reagents including antibodies or fragments thereof to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide $^{99m}$Tc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

Thus, the invention contemplates ECM protein binding reagents which may optionally be conjugated to a detectable label for use in the methods of the invention. In other aspects, the invention contemplates ECM protein binding reagents conjugated to an active agent. The active agent may be a detectable label as described above. Such compounds are useful in vitro or in vivo for detecting and characterizing tumor cells. The active agent may also be a drug or therapeutic such as an anti-cancer drug. Such compounds may be used as therapeutic conjugates to treat tumors.

The therapeutic conjugates include a binding reagent such as an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate). Other antitumor agents that can be conjugated to the binding reagents of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used in the conjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes.

For selective destruction of the cell, the antibody may be conjugated a highly radioactive atom. A variety of radioactive isotopes are available for the production of radioconjugated antibodies. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the conjugate is used for detection, it may comprise a radioactive atom for scintigraphic studies, for example $^{99m}$Tc or $^{123}$I, or a spin label for nuclear magnetic resonance (NMR) imaging (also known as magnetic resonance imaging, mri), such as $^{123}$I, $^{131}$I, $^{111}$In, $^{19}$F, $^{13}$C, $^{15}$N, 17O, Gadolinium, Manganese or Iron. The radio- or other labels may be incorporated in the conjugate in known ways. For example, the reagent may be biosynthesized or may be synthesized by chemical amino acid synthesis using suitable amino acid precursors involving, for example, fluorine-19 in place of hydrogen. Labels such as $^{99m}$Tc or $^{123}$I, $^{186}$Re, $^{188}$Re and $^{111}$In can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

Additionally, cytokines and antibody cytokine conjugates can be used therapeutically. Antibodies to the ECM proteins may be used to deliver cytokines which can have a number of functions including enhancing an immune response to the cancerous tissue. Cytokines include but are not limited to IL-2, IL-6, IL-8, IL-10, IL-12, IL-18, TNF, IFN-γ, IFN-β, chemokines, and IFN-α.

In one aspect, the invention provides methods for the treatment of cancer. The terms "tumor", "cancer", "cancerous tissue" and "carcinoma" are used interchangeably herein, and each, refers to an uncontrolled growth of cells which interferes with the normal functioning of the bodily organs and systems. Cancers, including those cancers which migrate from their original location and seed vital organs, can eventually lead to the death of the subject through the functional deterioration of the affected organs. Cancers can be classified into a variety of categories including, carcinomas, sarcomas and hematopoietic cancers. Carcinomas are malignant cancers that arise from epithelial cells and include adenocarcinoma and squamous cell carcinoma.

As used herein, a subject is a human, non-human primate, cow, horse, pig, sheep, goat, dog, cat, or rodent. In all embodiments human subjects are preferred. In aspects of the invention pertaining to predictive therapy in cancers, the subject is a human either suspected of having the cancer, or having been diagnosed with cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography. Diagnostic methods for cancer and the clinical delineation of cancer diagnoses are well known to those of skill in the medical arts.

In some aspects the specific ECM proteins identified herein may be utilized as a therapeutic target. These proteins can be targeted by specific reagents designed to interfere with their pro-metastatic functions and or expression. For example many of these proteins have specific receptors and therapeutic agents can be used to block the interactions of ECM proteins with their receptors or with other ECM proteins in order to treat cancer. Additionally, some of the ECM proteins are enzymes. Therapeutics may be used to interfere with the enzymatic activities of these proteins. Additionally, the expression of these proteins can be inhibited using inhibitory RNA, particularly when the RNA can be targeted to the tumor tissue. A therapeutic agent useful for blocking a protein-receptor or a protein-protein interaction is any type of reagent that binds to one or both of the proteins (receptor or ligand) and blocks the proteins from interacting. The reagent may be a protein, small molecule, nucleic acid or any other type of molecule which binds to and blocks the interaction, such as a receptor antagonist. For example the reagent may be (using antibodies, antibody fragments, peptides or peptidomimetics. Integrins as therapeutic reagents are described in, for example, Goodman and Picard, TIPS, 968, p. 1 (2012). Additionally anti-integrins, such as anti-integrin antibodies may be used as therapeutic reagents.

A therapeutic agent useful for blocking enzyme function is any reagent that interrupts the interaction or activity of the enzyme with it's substrate. For example the reagent may directly interfere with the interaction. For instance a structural antagonist of the substrate may compete for binding to the enzyme and block the interaction between the enzyme and substrate. Additionally the regent may indirectly interfere with the interaction by causing a conformational change or stability change in the enzyme which results in a loss of the enzymes ability to bind to the substrate or act on the substrate.

Methods for inhibiting the expression of genes encoding ECM proteins described herein are known in the art. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA or shRNA-mir expression constructs) are used to reduce expression of a gene encoding any of the ECM proteins described herein.

Examples of specific inhibitors of the ECM proteins described herein include, but are not limited to the inhibitors shown for each protein in the following Table.

| | |
|---|---|
| PLAT (tPA) | PAI-1, Ab-1 available commercially from Millipore or sodium phenylbutyrate |
| MMP1 | GM6001 MMP Inhibitor available commercially from Milliporeenzyme inhibitors exist candoxatril |
| MMP2 | anti-MMP-2 proform antibody available from commercially from Millipore; Candoxatril |
| CTSB | a2 macroglobulin |

-continued

| | |
|---|---|
| MMP19 | Candoxatril |
| EGLN1 | series of imidazo [1,2-a] pyridine derivatives cited in US2009176726A) |
| F10 | NSC12843701UPAC:4-(4-cyclohexylamino-9,10-dioxo-anthracen-1-yl)aminobenze-ne-sulfonic acid NSC125908P1UPAC:3-(9,10-dioxo-2-sulfo-anthracen-1-yl)diazenyl-2-hydroxy-b- enzoicacid NSC9600QIUPAC:4-[N'-(2-hydroxynaphthalen-1-y1)-N'-sulfo-hydrazino)benzene- sulfonicacid NSC13778JIUPAC:3-(3-stibonophenyl)prop-2-enoicacid 1NSC119110-U, NSC119111-V, NSC119913-X, NSC119915-Z, NSC170008-Y, and NSC306711-P) or (e.g., benthiavalicarb, dimethomorph, flumorph, iprovalicarb, mandipropamid, polyoxins, polyoxorim, prothiocarb, validamycin A, and valiphenal ) |
| F13b | Enzymatic inhibitors disclosed in U.S. Pat. No. 4,218,476 Antibodies disclosed in U.S. Pat. No. 5,620,688 |
| Vwf | Sulfobacins A and B, Anti-von Willebrand Factor Therapeutic Aptamer ARC1779 |
| LOX LOXL1 LoXL2 | inhibitor may be, for example, an antibody against LOX or LOXL, a small molecule inhibitor, siRNA, shRNA or an antisense polynucleotide against LOX or LOXL. The inhibitors may be noncompetitive inhibitors. (e.g. BAPN, pAPN) [AU2008282739AA] [Antibodies] (e.g., anti-LOXL2 monoclonal antibody GS-6634) |
| MMP9 | (e.g., Anti-MMP-9 Antibody nzyme inhibitors exist |
| MMP11 | candoxatril |
| MMP12 | candoxatril |
| PLOD2 | Anti-PLOD2 |
| ADAMDEC1 | Tamoxifen available commercially from Nolvadex |
| MMP12 | MMP-12 Inhibitor, MMP408; Anti-MMP-12 (C-terminus) Antibody and Anti-TIMP-1 Antibody AB770 available from commercially from Millipore; candoxatril |
| F2 | sulodexide, ximelagatran, warfarin, phenprocoumon, enoxaparin, ardeparin, fondaparinux, latamoxef, bacitracin, ticlopidine and erdosteine |
| CTSD | Serine Dependent Enzymes: These include such enzymes as Elastase (human leukocyte), Cathepsin G, Thrombin, Plasmin, C-1 Esterase, C-3-Convertase, Urokinase, Plasminogen activator, Acrosin, B-Lactamase, D-Alanine-D-Alanine Carboxypeptidase, Chymotrypsin, Trypsin and kallikreins. Thiol Dependent Enzymes: Cathepsin B. Carboxylic Acid Dependent Enzymes: These include such specific enzymes as Renin, Pepsin and Cathepsin D. Metallo Dependent Enzymes: These include Angiotensine Converting Enzyme, Enkephalinase, Pseudomonas Elastase and Leucine Aminopeptidase. (e.g. the compounds: CBZ-Val-Val-Phe-CF2-CO-Ala-laa CBZ-Val-Val-Phe-CF2H, CB Z-Val-Val-Phe-CF 3, CBZ-Val-Val-PheICF2-PhelAla-WH(CH2)2CH(cH3)2 CBZ-Val-Val-PhetCF2-Phe]Ala-NHcH2cH(cH3)2 laa being isoamyl amide |
| F9 | TAP, FIX, IXai |
| PLG | aminocaproic acid |

When used in combination with the therapies of the invention the dosages of known therapies may be reduced in some instances, to avoid side effects.

Cancer therapies and their dosages, routes of administration and recommended usage are known in the art and have been described in such literature as the *Physician's Desk Reference* (56th ed., 2002). In some embodiments, the therapeutic compounds of the invention are formulated into a pharmaceutical composition that further comprises one or more additional anticancer agents.

The active agents of the invention are administered to the subject in an effective amount for treating the subject. An "effective amount", for instance, is an amount necessary or sufficient to realize a desired biologic effect. For instance an effective amount is that amount sufficient to prevent or inhibit cancer cell growth or proliferation or alternatively an amount sufficient to induce apoptosis of a cancer cell or induce tumor regression. In some preferred embodiments the effective amount is that amount useful for reducing the development of metastatic cancers.

The effective amount of a compound of the invention in the treatment of a subject may vary depending upon the specific compound used, the mode of delivery of the compound, and whether it is used alone or in combination. The effective amount for any particular application can also vary depending on such factors as the type and/or degree of cancer in a subject, the particular compound being administered for treatment, the size of the subject, or the severity of the disorder. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity in and of itself and yet is entirely effective to treat the particular subject.

Toxicity and efficacy of the protocols of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays, animal studies and human studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

The diagnostic and therapeutic compounds described herein can be administered in combination with other therapeutic agents and such administration may be simultaneous or sequential. When the other therapeutic agents are administered simultaneously they can be administered in the same or separate formulations, but are administered at the same time. The administration of the other therapeutic agent, including chemotherapeutics can also be temporally separated, meaning that the therapeutic agents are administered at a different time, either before or after, the administration of the therapeutics described herein. The separation in time between the administration of these compounds may be a matter of minutes or it may be longer.

Thus, in some instances, the invention also involves administering another cancer treatment (e.g., radiation therapy, chemotherapy or surgery) to a subject. Examples of conventional cancer therapies include treatment of the cancer with agents such as All-trans retinoic acid, Actinomycin D, Adriamycin, anastrozole, Azacitidine, Azathioprine, Alkeran, Ara-C, Arsenic Trioxide (Trisenox), BiCNU Bleomycin, Busulfan, CCNU, Carboplatin, Capecitabine, Cisplatin, Chlorambucil, Cyclophosphamide, Cytarabine, Cytoxan, DTIC, Daunorubicin, Docetaxel, Doxifluridine, Doxorubicin, 5-fluorouracil, Epirubicin, Epothilone, Etoposide, exemestane, Erlotinib, Fludarabine, Fluorouracil, Gemcitabine, Hydroxyurea, Herceptin, Hydrea, Ifosfamide, Irinotecan, Idarubicin, Imatinib, letrozole, Lapatinib, Leustatin, 6-MP, Mithramycin, Mitomycin, Mitoxantrone, Mechlorethamine, megestrol, Mercaptopurine, Methotrexate, Mitoxantrone, Navelbine, Nitrogen Mustard, Oxaliplatin, Paclitaxel, pamidronate disodium, Pemetrexed, Rituxan, 6-TG, Taxol, Topotecan, tamoxifen, taxotere, Teniposide, Tioguanine, toremifene, trimetrexate, trastuzumab, Valrubicin, Vinblastine, Vincristine, Vindesine, Vinorelbine, Velban, VP-16, and Xeloda.

Multiple doses of the molecules of the invention are also contemplated. In some instances, when the molecules of the invention are administered with another therapeutic, for instance, a chemotherapeutic agent a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The compounds may be sterile or non-sterile.

The compounds described herein may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. In general, a pharmaceutical composition comprises the compound of the invention and a pharmaceutically acceptable carrier. Pharmaceutically acceptable carriers for nucleic acids, small molecules, peptides, monoclonal antibodies, and antibody fragments are well-known to those of ordinary skill in the art. As used herein, a pharmaceutically acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants, including those designed for slow or controlled release.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

The invention also encompasses binding reagents capable of interacting with ECM proteins, optionally in the form of conjugates, as described above. In some embodiments the binding reagent is an ECM protein binding reagent. The ECM protein binding reagents of the invention bind to an ECM protein, preferably in a selective manner. As used herein, the terms "selective binding" and "specific binding" are used interchangeably with respect to reagents to refer to the ability of the reagent to bind with greater affinity to ECM proteins and fragments thereof than to non-ECM proteins. That is, reagents that bind selectively to ECM proteins will not bind to non-ECM proteins to the same extent and with the same affinity as they bind to ECM proteins and fragments thereof. In some embodiments, the reagents of the invention bind solely to ECM proteins and fragments thereof. As used herein, a binding reagent that binds selectively or specifically to ECM proteins will bind with lesser affinity (if at all) to non-ECM proteins or other different ECM proteins. Lesser affinity may include at least 10% less, 20% less, 30% less, 40% less, 50% less, 60% less, 70% less, 80% less, 90% less, or 95% less.

The binding reagents useful according to the invention are isolated and include but are not limited to small molecules, isolated peptides, isolated antibodies and isolated antibody fragments. "Isolated peptides" as used herein refer to peptides that are substantially physically separated from other cellular material (e.g., separated from cells which produce the antibodies) or from other material that hinders their use either in the diagnostic or therapeutic methods of the invention.

The term "antibody" herein is used in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

ECM protein-antibodies are available commercially, from numerous sources including companies such as Abcam, AbD Serotec, Abnova, Thermo Scientific, Pierce Antibodies, Advanced Targeting Systems, Novus Bio, BD Pharmingen and many others. The commercial antibodies may be used as is or modified or humanized by methods well known to the skilled artisan.

The invention also includes kits made up of the various reagents described herein assembled to accomplish the methods of the invention. A kit for instance may include one or more reagents for detecting one or more ECM proteins or signatures of ECM proteins. The kit may further comprise assay diluents, standards, controls and/or detectable labels. The assay diluents, standards and/or controls may be optimized for a particular sample matrix. Reagents include, for instance, antibodies, nucleic acids, labeled secondary agents, or in the alternative, if the primary reagent is labeled, enzymatic or agent binding reagents which are capable of reacting with the labeled reagent. One skilled in the art will readily recognize that reagents of the present invention can be readily incorporated into one of the established kit formats which are well known in the art.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment or characterization of a cancer.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Methods

Tissue Preparation and ECM Protein Enrichment—

Sequential extractions of frozen samples of tissues or tumors were performed using the CNMCS (Cytosol/Nucleus/Membrane/Cytoskeleton) Compartmental Protein Extraction kit (Cytomol, Union City, Calif.) according to manufacturer's instructions. In brief, frozen tissues (150-200 mg) or tumors (200-j400 mg) were homogenized and extracted sequentially to remove (1) cytosolic proteins (2), nuclear proteins (3), membrane proteins (4), and cytoskeletal proteins leaving a final insoluble fraction enriched for ECM proteins. Fractions were separated on SDS-polyacrylamide gradient gels, transferred to nitrocellulose membranes and probed with antibodies to proteins characteristic of different subcellular compartments.

Mass Spectrometry—

ECM-enriched fractions were solubilized in urea, disulfide bonds reduced and alkylated, and proteins digested with PNGaseF, Lys-C, and trypsin. Solutions that began cloudy upon initial reconstitution were clear after overnight digestion. The resulting peptides were separated by off-gel electrophoresis (OGE) according to isoelectric point and by reversed-phase high-performance liquid chromatography followed by tandem mass spectrometry (MS/MS) on an LTQ Orbitrap mass spectrometer. Mass spectra were interpreted with SpectrumMill and annotated using the matrisome bioinformatics lists developed in this work. MS/MS spectra were searched against a UniProt database containing either mouse only or both mouse (53,448 entries) and human (78,369 entries) sequences; all sequences (including isoforms and excluding fragments) were downloaded from the UniProt web site. To each database a set of common laboratory contaminant proteins (73 entries) was appended. Peptides identified with a false discovery rate <2.5% were assembled into identified proteins, and an in silico protein list was then used to categorize all of the identified proteins as being ECM derived or not. MS/MS spectra searches allowed for carbamidomethylation of cysteines and possible carbamylation of N termini as fixed/mix modifications. Allowed variable modifications were oxidized methionine, deamidation of asparagine, pyro-glutamic acid modification at N-terminal glutamine, and hydroxylation of proline with a precursor shift range of −18 to 97 Da.

Bioinformatic Definition of Extracellular Matrix Proteins—

The human and mouse proteomes were each screened for proteins containing domains characteristic of ECM proteins, ECM-affiliated proteins, ECM modifiers and secreted factors. Those lists were subsequently screened to eliminate proteins that shared one or more of the defining domains but were not ECM or ECM-associated proteins based on other criteria. A webpage providing collection of resources (data files, sequence files) and further annotations on the bioinformatic pipeline developed according to these methods has been set up http://web.mit.edu/hyneslab/matrisome/. This site contains more detailed information on the methodology and is incorporated by reference.

Immunohistochemistry—

Tumor samples were formalin-fixed and paraffin-embedded. Sections were dewaxed and rehydrated following standard procedures. Antigen retrieval was performed by standard known methods. Sections were then blocked with PBS. Incubation with antibody was performed and secondary antibody incubation. Sections were counterstained to visualize nuclei.

Results:

ECM Protein Enrichment from Tissues—

Analysis of the protein composition of the extracellular matrix presents challenges due to the diversity, large size, insolubility and crosslinking of these proteins. By contrast, most other cellular components are soluble even at relatively low concentrations of salt or detergents. Therefore, we took advantage of the insolubility of ECM proteins to enrich for them while depleting other cellular components. We used a subcellular fractionation protocol to extract sequentially components from the cytosol, the nucleus, the membrane and the cytoskeleton and enrich for ECM proteins. ECM proteins such as fibronectin were not extracted during these intermediate steps and were found to be enriched in the final insoluble fraction.

Development of a Proteomics-Based Strategy to Characterize the Composition of ECM In Vivo—

To analyze the composition of the ECM-enriched fractions obtained after depletion of other cellular components, we digested the proteins to peptides and employed a proteomics pipeline using liquid chromatography combined with tandem mass spectrometry (LC-MS/MS) to identify peptides and proteins. Analysis by LC-MS/MS of ECM proteins enriched and digested to peptides confirmed a significant enrichment for matrix proteins, with more than 75% of the total precursor ion intensity (the sum of MS1 precursor ion peak areas for all identified peptides) corresponding to proteins defined as ECM. To help measure the success of our enrichment strategy and focus downstream biological follow-up we sought to categorize the identified proteins as being ECM-derived or not. The categorization of each protein identified by mass spectrometry was initially performed using the Gene Ontology (GO) "Cellular Compartment" annotations. However, this annotation showed several clear limitations. In order to interpret the mass spectrometric data we needed a better definition of which proteins should be considered as part of the ECM.

In Silico Definition of the ECM Proteins—

A Bioinformatic approach was developed to predict within any genome the ensemble of genes encoding what we define as the "matrisome," namely all those components constituting the extracellular matrix (the "core matrisome") and those components associated with it ("matrisome-associated" proteins). One hallmark of ECM proteins is their domain-based structure. Exploiting this characteristic, we established a list of 55 diagnostic InterPro domains commonly found in ECM proteins (type I, II and III fibronectin domains, type I thrombospondin repeats, laminin G domain, etc). This domain list was used to screen the UniProt protein database. We know that some of the domains used to select positively for ECM proteins are also found in transmembrane receptors and proteins involved in cell adhesion (growth factor receptors, integrins, etc) that do not belong to the ECM. These families of proteins also display a subset of specific domains (e.g. tyrosine kinase and phosphatase domains) and transmembrane domains incompatible with definition as "extracellular matrix" proteins. Therefore, a second step comprising a negative selection using 20 domains and a transmembrane domain prediction was used. This analysis was performed in parallel for both the mouse and human genomes and the respective murine and human matrisome lists were compared based on orthology. Manual curation of the matrisome lists also allowed us to add a very few known ECM proteins that do not contain any known domains; for example, dermatopontin and dentin sialophosphoprotein. Finally, knowledge-based annotation of these gene lists allowed us to define subcategories within the core matrisome; namely, ECM glycoproteins, collagens, and proteoglycans. The defined sets of core matrisome proteins are described herein and included in the signatures defined above.

Breast Cancer Analysis

Poorly metastatic (MDA-MB-231) or highly metastatic (LM2) human mammary carcinoma cells were orthotopically injected in immune-deficient mice NOD/SCID/IL2Rγ$^{-/-}$. The tumors formed were resected 6 weeks post-injection and the extracellular matrix of these tumors was extracted. The composition of the ECMs was determined for 2 independent tumors for each tumor type, by mass spectrometry. The comparison of the ECM composition of poorly and highly metastatic mammary tumor xenografts led to the definition of ECM signatures of each tumor type—GROUPS 1-3.

Colon Cancer Analysis

A panel of three samples: normal colon mucosa, colon tumor and liver metastasis was obtained for each of three human patients. To characterize the composition of the normal liver extracellular matrix (ECM), two pools of samples were generated from 4 and 5 healthy patients respectively. The ECM of these tissues and tumors was extracted and the composition of the ECMs was determined by mass spectrometry.

The comparison of the ECM composition of normal vs. tumor samples led to the identification of:

1) a set of proteins only detected in colon tumors (and in at least ⅔ patients) and not in any other tissues (normal colon, normal liver or liver met. samples)—GROUP 4

2) a set of proteins only detected in liver metastases (and in at least ⅔ patients) and not in any other tissues (normal colon, normal liver or colon tumor samples)—GROUP 5

3) an additional set of proteins was detected in at least ⅔ colon tumors and at least ⅔ liver metastases but not in the normal tissues.—GROUP 6

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of delivering an active agent to a tumor for treating or developing treatments, comprising
    administering to a colon cancer subject having a tumor binding reagents each of which interact specifically with an extracellular matrix (ECM) protein of a set of proteins characteristic of an ECM protein signature, wherein the binding reagents are conjugated to active agents in an effective amount to deliver the active agents to the tumor, wherein the signature ECM proteins includes at least 3 of the proteins selected from an ECM protein signature defined as being characteristic of metastatic primary colon carcinoma (group 4) but not including MMP9, MMP2, SPARC and/or TGFβ1, colon carcinoma metastases (group 5) but not including SPP1, metastatic colon carcinoma (primary & secondary) (group 6) but not including CTSB and/or S100A8, or a signature whose expression is associated with colon cancer or metastatic colon cancer (group 7) but not including MMP9, MMP2, SPARC, TGFβ1, SPPI, LOXL2, CTSB and/or S100A8.

2. The method of claim 1, wherein the binding reagent is an antibody or an antibody fragment.

3. The method of claim 1, wherein the tumor is metastatic.

4. A method of delivering an active agent to a tumor, comprising administering to a colon cancer subject having a tumor a binding reagent which interacts specifically with an extracellular matrix (ECM) protein, wherein the binding reagent is conjugated to an active agent in an effective amount to deliver the active agent to the tumor, wherein the ECM protein is a set of proteins characteristic of metastatic primary colon carcinoma (group 4): ADAMDEC1, ADAMTSL1, ANXA13, ANXA7, C15orf44, CLEC11A, COL8A1, CSPG4, EMID1, FCN1, FGL2, FMOD, GREM1, INHBE, LEFTY1, LEFTY2, LEPRE1, LOXL1, LTBP3, LTBP4, MATN2, MEGF8, MFAP4, MFGE8, MMP11, MMP12, MMRN1, MMRN2, MUC5B, PAPLN, PLOD2, PLOD3, PLXDC2, PLXNB2, PLXND1, S100A11, S100A14, S100A16, SERPINA3, SERPINF1, SVEP1, and THSD4.

5. A method of delivering an active agent to a tumor, comprising administering to a colon cancer subject having a tumor a binding reagent which interacts specifically with an extracellular matrix (ECM) protein, wherein the binding reagent is conjugated to an active agent in an effective amount to deliver the active agent to the tumor, wherein the ECM protein is a set of proteins selected from an ECM protein signature characteristic of colon carcinoma metastases (group 5): COMP, HPX, IGFALS, BMP1, C1QTNF5, FNDC1, ANXA3, C1QC, CCL21, COL10A1, COL15A1, COL27A1, CRLF3, CTSA, CTSH, CXCL12, F12, FCN3, HABP2, IL16, ITIH2, KNG1, LAMA3, LEFTY1, MMP12, MMP7, MST1, NID1, PCOLCE, PRG4, S100A12, S100A4, S100P, SERPINA1, SERPINA3, SERPINB5, SERPINB6, SERPINB9, SERPINC1, SERPIND1, and SERPING1.

6. A method of delivering an active agent to a tumor, comprising administering to a colon cancer subject having a tumor a binding reagent which interacts specifically with an extracellular matrix (ECM) protein, wherein the binding reagent is conjugated to an active agent in an effective amount to deliver the active agent to the tumor, wherein the ECM protein is a set of proteins selected from an ECM protein signature characteristic of metastatic colon carcinoma (primary and secondary (group 6): ANXA5, HCFC1, HTRA1, LTBP2, MXRA5, ST14, COL22A1, GPC4, PXDN, SFTPD, THBS2, C1QA, C1QB, F2, PLOD1, SERPINB1, AGRN, EFEMP2, HMCN1, SERPINE2, A2M, AEBP1, ANXA1, ANXA11, ANXA4, ANXA6, COL18A1, CTSD, ECM1, ELANE, F9, FCN1, HRG, IGFBP7, ITIH1, ITIH4, LAMB3, LAMC2, LGALS9, LMAN1, PLG, S100A11, S100A6, S100A9, SERPINF1, and SERPINH1.

7. A method of delivering an active agent to a tumor, comprising administering to a colon cancer subject having a tumor a binding reagent which interacts specifically with an extracellular matrix (ECM) protein, wherein the binding reagent is conjugated to an active agent in an effective amount to deliver the active agent to the tumor, wherein the ECM protein is a set of proteins selected from an ECM protein signature whose expression is associated colon cancer or metastatic colon cancer (group 7): CLEC11A, FGL2, LOXL1, MFGE8, MRN1, MUC13, PAPLN, PLOD3, PLXNB2, S100A16, ADAMTSL1, C15orf44, CSPG4, EMID1, FCN1, FMOD, LEFTY1, LEPRE1, MEGF8, MMP11, MMP12, MMRN2, PLOD2, PLXDC2, PLXND1, S100A11, S100A14, SERPINA3, SERPINF1, SVEP1, ADAMDEC1, ANXA13, ANXA7, COL8A1, GREM1, INHBE, LEFTY2, LTBP3, LTBP4, MATN2, MFAP4, MUC5B, THSD4, COMP, HPX, IGFALS, BMP1, C1QTNF5, FNDC1, ANXA3, C1QC, CCL21, COL10A1, COL15A1, COL27A1, CRLF3, CTSA, CTSH, CXCL12, F12, FCN3, HABP2, IL16, ITIH2, KNG1, LAMA3, LEFTY1, MMP12, MMP7, MST1, NID1, PCOLCE, PRG4, S100A12, S100A4, S100P, SERPINA1, SERPINA3, SERPINB5, SERPINB6, SERPINB9, SERPINC1, SERPIND1, SERPING1, ANXA5, HCFC1, HTRA1, LTBP2, MXRA5, ST14, COL22A1, GPC4, PXDN, SFTPD, THBS2, C1QA, C1QB, F2, PLOD1, SERPINB1, AGRN, EFEMP2, HMCN1, SERPINE2, A2M, AEBP1, ANXA1, ANXA11, ANXA4, ANXA6, COL18A1, CSTB, CTSD, ECM1, ELANE, F9, FCN1, HRG, IGFBP7, ITIH1, ITIH4, LAMB3, LAMC2, LGALS9, LMAN1, PLG, S100A11, S100A6, S100A9, SERPINF1, and SERPINH1.

8. The method of claim 1, wherein the active agent is a detectable label or a chemotherapeutic agent.

* * * * *